United States Patent [19]
Deluca et al.

[11] Patent Number: 5,536,713
[45] Date of Patent: Jul. 16, 1996

[54] 19-NOR-VITAMIN $D_3$ COMPOUNDS WITH SUBSTITUTENT AT 2-POSITION

[75] Inventors: Hector F. Deluca, Deerfield; Kato L. Perlman, Madison, both of Wis.; Rafal R. Sicinski, Warsaw, Poland

[73] Assignee: Wisconsin Alumni Research Foundation, Madison, Wis.

[21] Appl. No.: 406,646

[22] Filed: Mar. 20, 1995

Related U.S. Application Data

[63] Continuation of Ser. No. 42,994, Apr. 5, 1993, abandoned.

[51] Int. Cl.$^6$ .......................... A61K 31/59; C07C 401/00
[52] U.S. Cl. ............................................ 514/167; 552/653
[58] Field of Search ............................ 514/167; 552/653

[56] References Cited

U.S. PATENT DOCUMENTS

| | | |
|---|---|---|
| 4,666,634 | 5/1987 | Miyamoto et al. . |
| 5,237,110 | 8/1993 | DeLuca et al. . |
| 5,246,925 | 9/1993 | DeLuca et al. . |

FOREIGN PATENT DOCUMENTS

| | | |
|---|---|---|
| 0184206 | 6/1986 | European Pat. Off. . |
| 0387077 | 9/1990 | European Pat. Off. . |
| 0516410 | 12/1992 | European Pat. Off. . |

OTHER PUBLICATIONS

"Stereocontrolled Synthesis of a Trihydroxylated A Ring as an Immediate Precursor to $1\alpha,2\alpha,25$–Trihydroxyvitamin $D_3$", Posner et al, J. Org. Chem., 1991, No. 56, pp. 4339–4341.

"Chemistry of Synthetic High Polymers", Chem. Abstracts, 1989, vol. 110, No. 10, pp. 401–403.

"Regulatory Activities of $2\beta$–(3–Hydroxypropoxy)–1 alpha, 25–Dihydroxy–Vitamin $D_3$. A Novel Synthetic Vitmain $D_3$ Derivative, on Calcium Metabolism", Toshio Okano et al, Biochemical and Biophysical Research Communication, vol. 163, No. 3, 1989, pp. 1444–1449.

"Biologic Activity of Dihydroxylated 19–Nor–(Pre) Vitamin $D_3$", Roger Bouillon et al, Journal of Bone and Mineral Research, vol. 8, No. 8, 1993, pp. 1009–1015.

"Synthesis of 1alpha, 25–Dihydroxy–19–norprevitamin $D_3$", Luis A. Sarandeses et al, Tetrahedron Letters, vol. 33, No. 37, 1992, pp. 5445–5448.

"1alpha,25–Dihydroxy–19–Nor–Vitamin $D_3$, A Novel Vitamin D–Related Compound with Potential Therapeutic Acitivity", Kato L. Perlman, et al, Tetrahedron Letters, vol. 31, No. 13, 1990, pp. 1823–1824.

"Stereocontrolled Total Synthesis of 1alpha,25–Dihydroxycholecalciferol and 1alpha,25–Dihydroxyergocalciferol", Enrico G. Baggiolini et al, J. Org. Chem., 51, 1986, pp. 3098–3108.

"Chemical Conversion of Vitamin $D_3$ to its 1,25–Dihydroxy Metabolite", Jaroslaw et al, Tetrahedron Letters, vol. 32, No. 43, 1991, pp. 6057–6060.

*Primary Examiner*—Kimberly J. Prior
*Attorney, Agent, or Firm*—Andrus, Sceales, Starke & Sawall

[57] ABSTRACT

The $2\alpha$ and $2\beta$-hydroxy as well as the $2\alpha(3'$-hydroxypropoxy)- and $2\beta(3'$-hydroxypropoxy)- and $2\alpha$(benzyloxy)-analogs of 19-nor-$1\alpha,25$-dihydroxyvitamin $D_3$ are disclosed. The two 2-hydroxy analogs showed in vivo calcium transport with little or no bone calcium mobilization; the $2\beta$- more than the $2\alpha$- analog. Both analogs induced differentiation of malignant cells. The two analogs thus show promise in the treatment of osteoporosis. The $2\alpha$-hydroxypropoxy analog showed a selective activity profile, combining high potency in inducing differentiation of malignant cells with very low or no bone calcification activity, a possible use in the treatment of malignancies.

22 Claims, 4 Drawing Sheets

19-NOR-VITAMIN D₃ COMPOUNDS WITH SUBSTITUTENT AT 2-POSITION

This invention was made with United States Government support awarded by the National Institutes of Health (NIH), Grant No. DK-14881. The United States Government has certain rights in this invention.

This application is a continuation of application Ser. No. 08/042,994 filed Apr. 5, 1993, now abandoned.

This invention relates to biologically active vitamin $D_3$ compounds. More specifically, the invention relates to 19-nor-analogs of 1α-hydroxylated vitamin $D_3$ compounds having a substituent at the 2-position in the A-ring.

BACKGROUND AND SUMMARY OF THE INVENTION

The 1α-hydroxylated metabolites of vitamin D—most importantly 1α,25-dihydroxyvitamin $D_3$ and 1α,25-dihydroxyvitamin $D_2$—are known as highly potent regulators of calcium homeostasis in animals and humans, and more recently their activity in cellular differentiation has also been established. V. Ostrem et al, Proc. Natl. Acad. Sci. USA, (1987), 84, 2610. As a consequence, many structural analogs of these metabolites, such as compounds with different side chain structures, different hydroxylation patterns, or different stereochemistry, have been prepared and tested. Important examples of such analogs are 1α-hydroxyvitamin $D_3$, 1α-hydroxyvitamin $D_2$, various side chain fluorinated derivatives of 1α,25-dihydroxyvitamin $D_3$, and side chain homologated analogs. Several of these known compounds exhibit highly potent activity in vivo or in vitro, and some of these have been found to exhibit an interesting separation of activities in cell differentiation and calcium regulation. This difference in activity provides these compounds with advantageous therapeutic activity profiles and thus numerous of these compounds are in use, or have been proposed for use, in the treatment of a variety of diseases such as renal osteodystrophy, vitamin D-resistant rickets, osteoporosis, psoriasis, and certain malignancies.

Recently, a new class of vitamin D analogs has been discovered, i.e. the so-called 19-nor-vitamin D compounds. 19-Nor-vitamin D compounds are vitamin D analogs in which the ring A exocyclic methylene group (carbon 19) typical of all vitamin D compounds has been removed and replaced by two hydrogen atoms. Specifically, these compounds exhibit a selective activity profile with high potency in inducing cellular differentiation, and minimal bone calcification activity. Such a differential activity profile renders these compounds useful for the treatment of malignancies, or the treatment of various skin disorders. Two different methods of synthesis of these 19-nor-vitamin D analogs have been described (Perlman et al. Tetrahedron Letters 31, 1823 (1990); Perlman et al Tetrahedron Letters 32., 7663 (1991), and DeLuca et al U.S. Pat. No. 5,086,191).

In U.S. Pat. No. 4,666,634, 2β-hydroxy and alkoxy analogs of 1α,25-dihydroxyvitamin $D_3$ have been described and examined as potential drugs for osteoporosis and as antitumor agents See also T. Okano et al, Biochem. and Biophys. Res. Comm., (1989) 163, 1444. However the new analogs also have many undesired side effects most notable of which is the potential development of hypercalcemia upon administration.

In a continuing effort to explore the new 19-nor class of pharmacologically important vitamin D analogs, the 2α- and 2β-hydroxy as well as the 2α(3'-hydroxypropoxy)- and the 2β(3'-hydroxypropoxy)- and 2α(benzyloxy)-analogs of 19-nor-1α,25-dihydroxyvitamin $D_3$ have now been synthesized. The two 2-hydroxy analogs showed in vivo calcium transport with little or no bone calcium mobilization; the 2β- more than the 2α- analog. Both 2-hydroxy analogs induced differentiation of malignant cells. These two analogs thus show promise in the treatment of osteoporosis. The 2α-hydroxypropoxy analog showed a selective activity profile, combining high potency in inducing differentiation of malignant cells with very low bone calcium mobilizing activity, a possible use in the treatment of cancer.

DISCLOSURE OF THE INVENTION

Figure 1A:
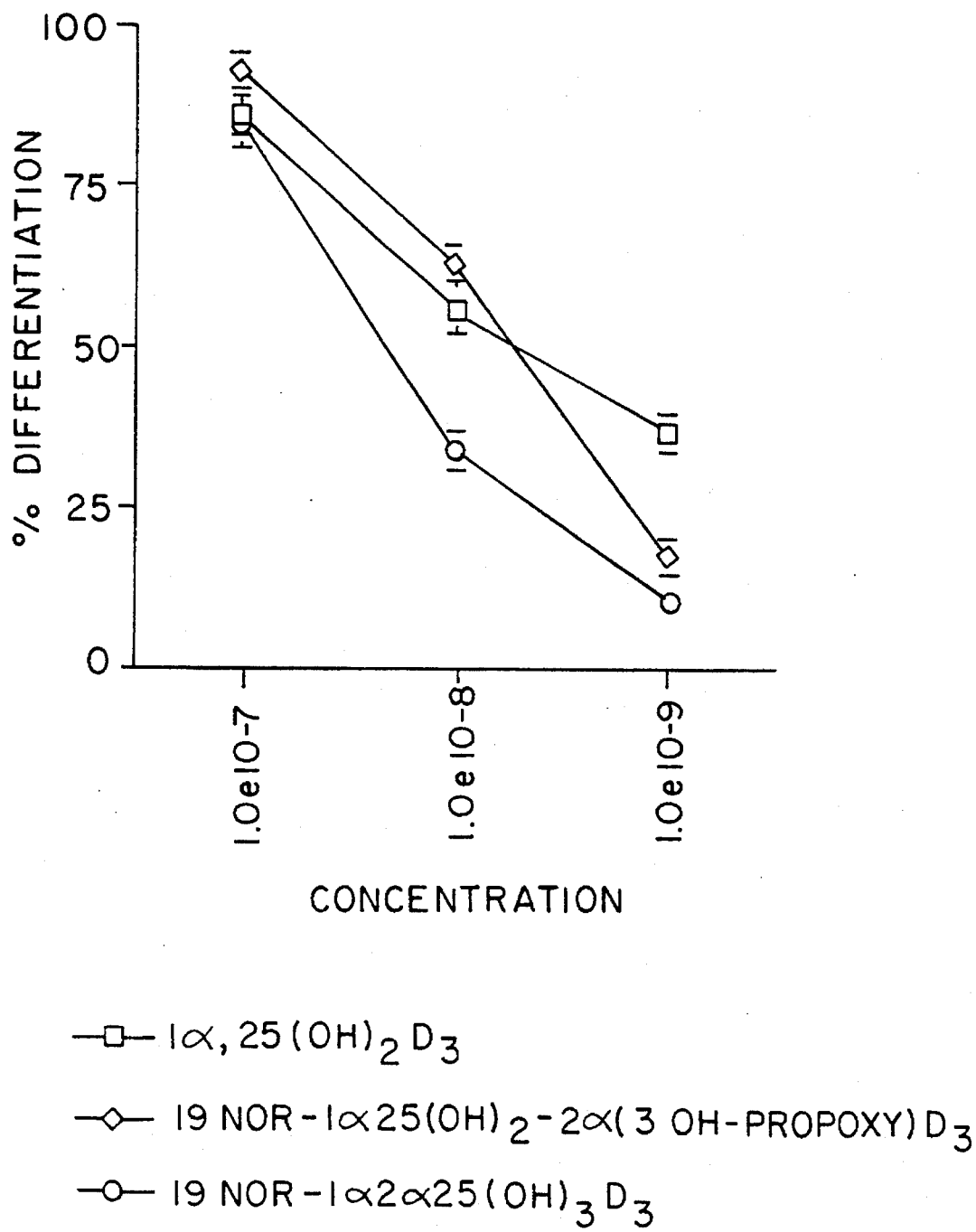
FIGS. 1a and 1b are graphs of the percent differentiation of HL-60 cells versus concentration for a prior art vitamin $D_3$ compound and three of the new 19-nor-vitamin $D_3$ compounds.

The new 19-nor-Vitamin $D_3$ analogs having a substituent at the 2-position in the A-ring are represented by the following general formula:

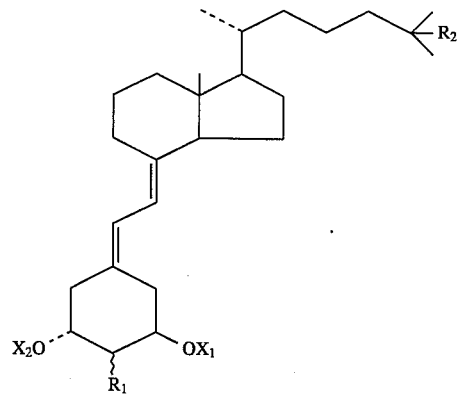

where $X_1$ and $X_2$ are each selected from hydrogen or a hydroxy protecting group. $R_1$ which may be in either α or β position is a hydroxy group, protected hydroxy group or the group $OR_3$ where $R_3$ is an alkyl, hydroxyalkyl, fluoroalkyl, arylalkyl or aryl group, and $R_2$ is hydrogen or a hydroxy group. Specific examples of the compounds represented by the formula above are: 1α,2α,25-trihydroxy-19-nor-vitamin $D_3$; 1α,2β,25-trihydroxy-19-nor-vitamin $D_3$; 1α,25-dihydroxy-2β-(3'-hydroxypropoxy)-19-nor-vitamin $D_3$; 1α,25-dihydroxy-2β-(3'-hydroxypropoxy)-19-nor-vitamin $D_3$ and 1α,25-dihydroxy-2α(benzyloxy)-19-nor-vitamin $D_3$.

The starting material for the synthesis of these new 19-nor compounds is the commercially available synthon (1R,3R, 4R,5R) (–) quinic acid, D. Desmaele et al, Tetrahedron Letters (1985) 26, 4941, which after esterification with methanol in the presence of catalytic amount of p-toluene sulfonic add, followed by treatment with tert-butyldimethylsilyl chloride and triethylamine in dimethyl formamide gave the protected methyl ester 1. Reduction with diisobutylaluminum hydride gave polyalcohol 2 followed by sodium periodate oxidation to the cyclohexanone derivative 3. The 4-hydroxy group was protected with N-(trimethylsilyl) imidazole to give 4. The trimethylsilyl protecting group in this particular case with the very hindered 2-hydroxy group gave the needed chemoselectivity in the 2 position throughout all subsequent steps. Peterson reaction with methyl (trimethylsilyl)acetate in the presence of LDA in anhydrous tetrahydrofuran gave a mixture of the protected cyclohexylidene esters 5a, 5b. The latter was reduced to the allylic alcohols 6a, 6b with diisobutylaluminum hydride and separated and finally transformed to the desired phosphine oxide 7a and 7b by in situ conversion to the tosylate with BuLi and tosylchloride followed by lithium diphenylphosphide and oxidation with hydrogen peroxide. (During all these steps the 2 trimethylsilyloxy group was not removed).

The synthesis of the CD ring Windaus Grundmann ketone with the appropriate protected side chain is well documented in the literature. See E. G. Baggiolini et al, J. Org. Chem. (1986) 51, 3098; F. J. Sardina et al, J. Org. Chem. (1986) 51 1264; and U.S. Pat. No. 4,804,502. In the present disclosure, the recently described procedure i.e. ozonolysis followed by $RuO_4$ oxidation of commercial vitamin $D_3$ was chosen. See J. Kiegiel et al, Tetrahedron Letters 32, 6057 (1991). The 25-OH of the Grundmann ketone was protected with TES-Cl, imidazole, in DMF to give chemoselectivity from the 2-OTMS group in the 19-nor product. With the required synthons on hand, the final convergent formation of 19-nor-1α,2α and -2α,25-dihydroxy-cholecalciferol 9a, 10a was then accomplished. See B. Lythgoe et al, J. Chem. Soc. Perkin Trans. 1, (1978) 590; B. Lythgoe et al, J. Chem. Soc. Perkin Trans 1, (1976) 2386; and H. T. Toh et al, J. Org. Chem. (1983), 48, 1414. Wittig Horner reaction of the lithium phosphinoxy carbanion prepared from 7a and n.butyl lithium at −78° C. in tetrahydrofuran with the protected Windaus Grundmann ketone 8 proceeded to give the desired 19-nor-vitamin derivative 9a which after deprotection gave the crystalline 19-nor-1α,2α,25-trihydroxyvitamin $D_3$ 10a; 10b was obtained in the same manner from 7b.

For the synthesis of the 19-nor-2α(3'-hydroxypropoxy)-1α,25-dihydroxyvitamin $D_3$ 14a,9a was partially hydrolyzed under carefully controlled conditions: i.e. 9a was treated with a mixture of 8:8:1 tetrahydrofuran acetic acid water at room temperature for 4.5 h and the resulting mixture separated by HPLC to give the free 2α-hydroxy 11a. 3-bromo-1-tert.butyldimethylsilyloxy propane 12 was chosen as the alkylating agent and was prepared by silylation from the corresponding bromo alcohol. 11a was treated with sodium hydride and the protected bromo compound 12 in the presence of 18-Crown-6 in anh. DMF for 48 h to give the protected 13a which was deprotected with $Bu_4NF$ in THF to give the expected 14a; 14b was obtained in the same manner from 11b. Under the same conditions 11a with benzylbromide gave after deprotection 16a.

The stereochemistry at the 2-position of 5 was determined first by separation of the enantiomers followed by partial hydrolysis, and acylation. The two enantiomer's structure was then determined by NOE followed by 2D NMR in deuterated benzene. This revealed that under the reaction conditions the major component was the 2α-compound 5a and the minor the 2β-compound 5b (3:1).

As used in the description, and in the claims, the term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkyl or arylsilyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl," "fluoroalkyl" and "arylalkyl" refer to such an alkyl radical substituted by one or more hydroxy, fluoro or aryl groups respectively. An "acyl" group is an alkanoyl group of 1 to 6 carbons in all its isomeric forms, or an aroyl group, such as benzoyl, or halo-, nitro- or alkyl-substituted benzoyl groups, or an alkoxycarbonyl group of the type alkyl-O-CO-, such as methoxycarbonyl, ethoxycarbonyl, propyloxycarbonyl, etc., or a dicarboxylic acyl group such as oxalyl, malonyl, succinoyl, glutaroyl, or adipoyl. The term "aryl" signifies a phenyl-, or an alkyl-, nitro- or halo-substituted phenyl group. The term alkoxy signifies the group alkyl-O-.

This invention is more specifically described by the following illustrative examples. In these examples specific products identified by Arabic numerals (e.g. 1, 2, 3, etc.) refer to the specific structures so identified in the preceding description and in the Schemes.

EXAMPLE 1

Preparation of 1α,2α,25-trihydroxy-19-nor-vitamin $D_3$ (10a) and 1α,2β,25-trihydroxy-19-nor-vitamin $D_3$ (10b).

(a) (1R,3R,4R,5R)(−) Methyl Quinicate.

Referring first to Scheme I, p-toluene sulfonic acid (0.5 g) was added to a solution of quinic acid (12.74 g, 66.3 mmol) in methanol. The solution was stirred for 24 h. Solid $NaHCO_3$ (1.0 g) was added and after 15 min the solution was filtered and concentrated to give 12.61 g (61.16 mmol) of the methyl ester in 92% yield.

(b) (1R,3R,4R,5R) Methyl 3,5-Bis(tert-butyldimethylsilyloxy). 1,4- dihydroxycyclohexane-carboxylate (1).

tert-Butyldimethylsilyl chloride (6.73 g, 44.62 mmol) was added to a solution of methyl (1R,3R,4R,5R)(−) quinicate (3.68 g., 17.85 mmol) and triethyl amine (6.2 mL, 44.62 mmol) in 44 mL or anhydrous dimethyl formamide at 0° C. with stirring. After 4 h the solution was warmed to room temperature and stirring continued for another 14 h. The solution was poured into water and extracted with ether. The combined organic layers were extracted with brine, dried over anhydrous $MgSO_4$, filtered and concentrated. The residue was purified by column chromatography on silica gel, eluting with 5–10% ethyl acetate in hexane mixtures, to give 4.6 g (60%) of 1 as a white solid. M.p. 82°–82.5° C. (after recrystallization from hexanes). $^1$H NMR ($CDCl_3$, 500 MHz) δ 4.53 (bs, 1 H), 4.36 (bs, 1 H), 4.11 (ddd, 1 H), 3.76 (s, 3 H), 3.42 (dd, 1 H), 2.31 (bs, 1 H), 2.18 (bd, 1 H), 2.05 (ddd, 2 H), 1.82 (dd, 1 H), 0.91 (s, 9 H), 0.89 (s, 9H) 0.15 (s, 3 H), 0.14 (s, 3 H), 0.11 (s, 3 H), 0.09 (s, 3 H) MS m/e (relative intensity) 377 (70), 227 (91).

(c) (1R,3R,4R,5R) [3,5-Bis(tert,-butyldimethylsilyloxy]-1, 4-dihydroxy]-1-hydroxymethylcyclohexane (2).

Diisobutyl aluminum hydride (45 mL, 45.0 mmol, 1.0M in hexanes) was added to a solution of the ester (3.26 g, 7.5 mmol) in ether (45 mL) at −78° C. After 20 min. the solution was warmed to −23° C. and stirred for 2 h. The solution was diluted with ether and then 2N potassium sodium tartrate was slowly added. The solution was warmed to room temperature and stirred for 15 min. The ether layer was separated and the aqueous layer extracted with ether. The combined ether layers were extracted with brine, dried over anh. $MgSO_4$, filtered and concentrated. The material was further purified by column chromatography on silica gel with 25% ethyl acetate/hexanes to give 83% of 2 (2.52 g, 6.20 mmol). Mp. 108°–109° C. from hexanes. $^1$H NMR (CDCl$_3$, 500 MHz) δ 4.52 (bs, 1 H), 4.32 (bs, 1 H), 4.12 (ddd, 1 H), 3.40 (dd, 1 H), 3.33 (dd, 2 H), 2.28 (d, 1 H), 2.11 (dd, 1 H), 2.00 (ddd, 2 H), 1.52 (dd, 1 H), 1.33 (dd, 1 H), 0.91 (s, 9 H), 0.90 (s, 9 H), 0.16 (s, 3 H), 0.14 (s, 3 H), 0.12 (s, 3 H), 0.11 (s, 3 H), MS m/e (relative intensity): 349 (8), 331 (13), 239 (12), 199 (100).

(d) (3R,5R) [3,5-Bis(tert.-butyldimethylsilyloxy), 4-hydroxy]-1-cyclohexanone (3).

Sodium periodate saturated water (28.5 mL) was added to the triol 2 (1.91 g, 4.7 mmol) in methanol (124 mL) at 0° C. The solution was stirred for 1 h, then poured into water and extracted with ether. The combined ether fractions were washed with brine, dried over anhydrous MgSO$_4$, filtered and concentrated, to give 1.72 g (4.59 mmol) of 3 (98%). No further purification was required. Mp. 98°–100° C. from hexanes. $^1$H NMR (CDCl$_3$, 500 MHz) δ 4.28 (m, 2 H), 3.80 (bs, 1 H), 2.77 (dd, 1 H, J=14.3, 3.4 Hz), 2.59 (dd, 1 H, J=13.1, 10.7 Hz), 2.45 (dd, 1 H, J=14.1, 5.2 Hz), 2.25 (bd, 1 H, J=15.9 Hz), 0.90 (s, 9 H), 0.85 (s, 9 H), 0.08 (s, 3 H), 0.08 (s, 3 H), 0.06 (s, 6 H), MS m/e (relative intensity) 317 (62), 231 (16), 185 (76), 143 (100).

(e) (3R,5R) [3,5-Bis (tert.-butyldimethylsilyloxy)-4-tri-methylsilyloxy]-1-cyclohexanone (4).

N-(Trimethylsilyl)imidazole (2.52 mL, 26.67 mmol) was added to a solution of the ketoalcohol 3 (1.56 g, 4.167 mmol) in methylene chloride (38 mL). The solution was stirred for 20 h. Water (1 mL) was added and the solution stirred for 30 min. Brine and methylene chloride was added. The brine was extracted with methylene chloride. The combined methylene chloride fractions were dried with anh. MgSO$_4$, filtered and concentrated. The residue was further purified by column chromatography on silica gel with 10% ethyl acetate in hexane to give 4 (1.76 g, 3.95 mmol) in 95% yield. $^1$H NMR (CDCl$_3$, 500 MHz) δ 4.25 (m, 1 H), 4.13 (m. 1 H), 4.04 (m, 1 H), 2.74 (ddd, 2 H), 2.38 (dd, 1 H), 2.19 (dd, 1 H), 0.90 (s, 9 H), 0.86 (s, 9 H), 0.16 (s, 9 H), 0.07 (bs, 12 H). MS m/e (relative intensity): 431 (5), 389 (100), 299 (45), 257 (28).

(f) (S)-and (R)-(3R,5R) Methyl [3,5-bis(tert.-butyldimethylsilyloxy)-4-hydroxy]-cyclohexylidene carboxylate (5a and 5b).

n.Butyl lithium (2.3 mL, 3.0 mmol) 1.3M in hexanes was added to a solution of diisopropylamine (0.42 mL, 3.0 mmol) in anhydrous tetrahydrofuran (2.0 mL) under argon at −78° C. with stirring and methyl (trimethylsilyl) acetate (0.49 mL, 3.0 mmol) was added. After 15 min the protected keto compound 4 (0.629 g, 1.4 mmol) in anhydrous tetrahydrofuran (2.0+1 mL) was added. The solution was stirred for 2 h at −78° C. The reaction mixture was quenched with saturated ammonium chloride solution and extracted with ether. The combined ether fractions were washed with brine, water and dried over anhydrous MgSO$_4$, filtered and evaporated. The product was further purified by SepPak filtration in 5% ethyl acetate in hexane to give 0.693 g (98%) of a mixture of the two stereoisomer allylesters 5a and 5b. For analytical purposes the two allylesters were separated by HPLC (1% ethyl acetate in hexane, Zorbax Sil 10×25 cm, with differential refractometer as detector.) 5a Peak II (Major) (S): $^1$H NMR (CDCl$_3$, 500 MHz) δ 0.04, 0.05, 0.08 (3H, 3H and 6H, each s, 4× SiMe), 0.13 (9H, s, SiMe$_3$), 0.86 (9H, s, Si-t-Bu), 0.89 (9H, s, Si-t-Bu), 2.00 (1H, dd, J=13.5, 4.7 Hz, 6β-H), 2.60 (1H, br d, J~13.5 Hz, 6α-H), 2.74 and 3.28 (1H and 1H, each br m, 2-H$_2$), 3.62 (1H, narrow m, 4β-H), 3.68 (3H, s, OMe), 3.86 (1H, ~q, J~4 Hz, 5α-H), 3.95 (1H, dt, J=9.5, 2.5 Hz, 3β-H), 5.63 (1H, s, 7-H). 5b Peak 1 (minor) (R): $^1$H NMR (CDCl$_{13}$, 500 MHz) δ 0.04, 0.05, 0.06 (3H, 3H and 6H, each s, 4× SiMe), 0.13 (9H, s, SiMe$_3$), 0.84 (9H, s, Si-t-Bu), 0.89 (9H, s, Si-t-Bu), 2.12 (1H, dd, J=12.7, 3.8 Hz, 6α-H), 2.57 (1H, br t, J~12 Hz, 6β-H), 2.62 and 3.35 (1H and 1H, each br d, J~13 Hz, 2-H$_2$), 3.65 (1H, narrow m, 4α-H), 3.66 (3H, s, OMe), 3.86 (1H, ~q, J~4 Hz, 3β-H), 3.99 (1H, dt, J=9.9, 3.7 Hz, 5α-H), 5.70 (1H, s, 7-H).

(g) (S)- and (R)-(3R,5R) [3,5-Bis(tert.-butyldimethylsilyloxy) (4-trimethylsilyloxy)-cyclohexylidene] ethanol (6a and 6b).

A solution of 410 mg of mixture of esters 5a, 5b (0.82 mmol) in 8 mL of anhydrous toluene was treated at −78° C. under argon with 7 mL (10.5 mmol) of a 1.5M solution of diisobutylaluminum hydride in toluene. After the addition stirring was continued for 1 h at −78° C. The reaction mixture was then quenched by the addition of 2N potassium sodium tartrate, the organic phase was separated, and the aqueous phase extracted with ethyl acetate. The combined organic phases were washed with water and brine and dried over anhydrous MgSO$_4$, filtered and evaporated. The residue was purified by fast filtration through a silica gel column, using 20% ethyl acetate in hexane as eluent, to give 352 mg (91%) alcohols 6a and 6b which were separated by HPLC, Zorbax Sil 10×25 cm column, 10% ethyl acetate in hexane. First eluted the minor 4R alcohol (42 mg) 6b followed by the major 4S alcohol 6a (188 mg) (61% recovery). 6a Peak II (major) (S): $^1$H NMR (CDCl$_3$, 500 MHz) d 0.04, 0.05, 0.06, 0.07 (3H, each s, 4× SiMe), 0.13 (9H, s, SiMe$_3$), 0.87 and 0.89 (9H and 9H, each s, 2× Si-t-Bu), 1.93 (1H, dd, J=13.5, 5.5 Hz, 6β-H), 2.24 (1H, br d, J~12.6 Hz, 2β-H), 2.38 (1H, dd, J=12.6 Hz, 9.2 Hz, 2α-H), 2.50 (1H, dd, J=13.5, 3.5 Hz, 6α-H) 3.57 (1H, narrow m, 4β-H), 3.80 (1H, dt, J=3.5 Hz, 5.5 Hz, 5α-H), 3.89 (1H, ddd, J=9.2, 3.0, 2.6 Hz, 3β-H), 4.13 (2H, m, 8-H$_2$), 5.45 (1 H, t, J=6.9 Hz, 7-H). 6b Peak I (minor) (R): $^1$H NMR (CDCl$_3$, 500 MHz) δ 0.06, 0.07 (6H and 6H, each s, 2× SiMe$_2$), 0.13 (9H, s, SiMe$_3$), 0.87 and 0.89 (9H and 9H, each s, 2× Si-t-Bu), 2.06(1H, dd, J=12.3, 3.9 Hz, 6α-H), 2.23 (1H, dd, J=13.6, 4.0 Hz, one of 2-H$_2$), 2.38 (1H, br d, J=13.6 Hz, one of 2-H$_2$), 2.45 (1H, br t, J~11 Hz, 6β-H), 3.62 (1H, dd, 4.0 and 2.0 Hz, 4α-H), 3.82 (1H, ~q, J~4 Hz, 3β-H), 3.89 (1H, ddd, J=10, 4 and 2 Hz, 5α-H), 4.03 and 4.12 (1H and 1H, each br m, 8-H$_2$), 5.57 (1H, t, J=7.1 Hz, 7-H).

(h) (S)- and (R)-(3R,5R)-[3,5-Bis(tert.-butyldimethylsilyloxy-4-trimethylsilyl)-cyclohexylidenel ethyl diphenylphosphine oxide (7a and 7b).

265 mg dry allylalcohol 6a (0.56 mmol) was dissolved in 5.0 mL anhydrous tetrahydrofuran and 0.35 mL (0.56 mmol) n. Butyl lithium (1.6M in hexanes) added under argon. 106 mg (0.56 mmol) recrystallized dry tosylchloride was dissolved in 1.0 mL anhydrous tetrahydrofuran and added to the allylalcohol-BuLi solution under argon at 0° C. The solution was stirred at 0° C. for 5 min. and set aside at 0° C.

In another dry flask with air replaced by argon 350 μl (0.56 mmol) n.Butyl lithium (1.6M in hexanes) was added to 100 μl (0.56 mmol) diphenylphosphine in 200 μl anhydrous tetrahydrofuran at 0° C. with stirring under argon. To the orange solution was syphoned under argon pressure at 0° C. the tetrahydrofuran solution of the allylic tosylate. The resulting orange solution was stirred an additional 30 min at 0° C. and quenched by the addition of water. Solvents were evaporated under reduced pressure and the residue was dissolved in 5 mL of dichloromethane. The dichloromethane layer was stirred with 20 mL of 10% hydrogen peroxide at 0° C. for 1 h. The dichloromethane layer was separated and washed with cold aqueous sodium sulfite, water and brine, dried over anhydrous MgSO$_4$, filtered and evaporated. The residue was dissolved in 20% 2-propanol in hexane and passed through a silica SepPak and purified by HPLC (Zorbax-Sil 9.4×25 cm column, 20% 2-propanol in hexane) to give 220 mg (60%) of the crystalline phosphine oxide 7a. 7a UV (EtOH): $\lambda_{max}$ 258, 265, 272 nm. $^1$H NMR (CDCl$_3$, 500 MHz) δ-0.02, 0.00, 0.01, 0.03 (3H, each s, 4× SiMe), 0.09 (9H, s, SiMe$_3$), 0.83 and 0.87 (9H and 9H, each s, 2× Si-t-Bu), 1.86 (1H, br d, J~13.5 Hz, one of 6-H$_2$), 1.99 and 2.08 (1H and 1H, each m, 2-H$_2$), 2.42 (1H, br d, J~13.5 Hz, one of 6-H$_2$), 3.10 (2H, m, 8-H$_2$), 3.51 (1H, narrow m, 4β-H), 3.72 (1H, dt, J=3.7, 5.2 Hz, 5αH), 3.81 (1H, ddd, J=8.8, 4.2, 2.4 Hz, 3β-H), 5.24 (1H, q, J=6.9 Hz, 7-H), 7.46, 7.52 and 7.71 (4H, 2H and 4H, each m, Ar-H). Mass spectrum (exact mass calcd for C$_{35}$H$_{59}$O$_4$Si$_3$P 658.3459 found 658.3453), m/e (relative intensity) 658 (M+, 1), 643 (3), 601 (100), 526 (12), 469 (43). 7b was prepared in the same way as 7a except from the corresponding 6b. 7b $^1$H NMR (CDCl$_3$, 500 MHz) δ 0.02, (12 H, s, 2× SiMe), 0.09 (9H, s, SiMe$_3$), 0.85 (18 H, s, 2× Si-t-Bu), 1.88 (1H, br d, J~14 Hz, one of 2-H$_2$), 2.01 (1H, br d J~12 Hz, 6α-H), 2.06 (1H, br d, J~14 Hz, one of 2-H$_2$), 2.34 (1H, br m, 6β-H) 3.02 and 3.14 (1 H and 1 H, each br m, 8-H$_2$), 3.51 (1H, narrow m, 4α-H), 3.71 (1H, ~q, J=4.4 Hz, 3β-H), 3.84 (1H, m, 5α-H, 5.27 (1H, m, 7-H), 7.46, 7.52 and 7.71 (4H. 2H and 4H, each m, Ar-H).

(i) Triethylsilyloxy Grundmann Ketone (8).

Referring now to Scheme II, the CD-ring fragment for the 19-nor vitamin D-derivative was prepared by ozonolysis of commercial vitamin D$_3$ to provide 20 followed by RuO$_4$ oxidation to give the 25-hydroxy-Grundmann ketone 21. To 30 mg ketone 21 (0.1 mmol) and 28 mg imidazole (0.41 mmol) in 500 μl anhydrous dimethyl formamide was added 40 μl triethylsilyl chloride (0.24 mmol). The mixture was stirred at room temperature for 2 h. Ethyl acetate was added and water, and separated. The ethyl acetate layer was washed with water, brine, dried over anh. MgSO$_4$, filtered and evaporated. The residue was passed through a silica gel ScpPak column in 10% ethyl acetate in hexane, and after evaporation purified by HPLC (Zorbax Sil 9.4×25 cm column, 10% ethyl acetate in hexane, using a differential refractometer) to give 31 mg (79%) of the pure protected ketone 8. $^1$H NMR (CDCl$_3$, 500 MHz) δ 0.56 (6H, q, J=8.0 Hz, 3 × Si-CH$_2$), 0.64 (3H. s, 18-H$_3$), 0.94 (9H, t, J=8.0 Hz, 3 × SiEt), 0.95 (3H, d, J=6.5 Hz, 21-H$_3$), 1.19 (6H, br s, 26- and 27-H$_3$), 2.45 (1H, dd. J=11.7, 7.4 Hz, 14α-H).

(j) 1α,2α,25-trihydroxy-19-nor-vitamin D$_3$ (10a).

16.9 mg (25.7 μmol) phosphine oxide 7a was dissolved in 200 μl anhydrous tetrahydrofuran, cooled to 0° C. and 20 μl (26 μmol) n.butyl lithium (1.3 molar in hexanes) added under argon with stirring. The solution turns deep orange. The mixture was cooled to −78° C. and 7.5 mg (21 μmol) protected ketone 8 added in 200 μl+100 μl anhydrous tetrahydrofuran. The mixture was stirred under argon at −78° C. for 1 h (at that time the solution became colorless) and at RT 18 hr. Ethyl acetate was added and the organic phase washed with water, brine, dried over anhydrous MgSO$_4$, filtered and evaporated. The residue was dissolved in 10% ethyl acetate in hexane, passed through a silica SepPak and washed with 40 mL of the same to give the 19-nor vitamin D derivative 9a. The Sep Pak was then washed with 20% 2-propanol in hexane to recover 5 mg unchanged diphenylphosphine oxide. 9a was purified by HPLC in 10% ethyl acetate in hexane (Zorbax Sil 9.4×25 cm column) to give 8.2 mg of the protected 19-nor vitamin D$_3$ derivative 9a (54%). $^1$H NMR (CDCl$_3$, 500 MHz) δ 0.04, 0.05, 0.06 (3H, 3H, and 6H, each s, 4× SiMe), 0.12 (9H, s, SiMe$_3$), 0.55 (3H, s, 18-H$_3$), 0.56 (6H, q, J=7.4 Hz, 3 × SiCH$_2$), 0.87 and 0.88 (9H and 9H, each s, 2 × Si-t-Bu), 0.92 (3H, d, J=6.1 Hz, 21-H$_3$), 0.95 (9H, t, d=7.4 Hz, 3 × SiEt), 1.19 (6H, br s, 26- and 27-CH$_3$), 2.79 (1H. br d, J=12.6 Hz, 9β-H), 3.53 (1H, m, 2β-H), 3.80 (1 H, m, 3α-H), 3.88 (1 H, m, 1β-H), 5.81 and 6.10 (1 H and 1 H, each d, J=11.4 Hz, 6- and 7-H). Mass spectrum (exact mass calcd for C$_{47}$H$_{94}$O$_4$Si$_4$ 834.6229, found 834.6241) m/e (relative intensity) 834 (12), 805 (3), 702 (100), 645 (18), 599 (45). All of 9a was dissolved in 1.0 ml of anhydrous tetrahydrofuran and treated with 150 μl of a 1M solution of tetrabutylammonium fluoride in tetrahydrofuran. The mixture was stirred under argon at RT for 16 h and extracted with ethyl acetate. The organic phase was washed with 10% NaHCO$_3$ solution, brine and dried over anhydrous MgSO$_4$, filtered and evaporated. The residue was filtered through a Silica SepPak and purified by HPLC (Zorbax Sil 9.4×25 cm column, 30% 2-propanol in hexane) to give 1.48 mg of pure 1α,2α,25-trihydroxy-19-nor-vitamin D$_3$ 10a. UV (in EtOH) $\lambda_{max}$: 243, 251.5, 261 nm. Mass spectrum m/e (relative intensity): 420 (M+, 100), 402 (55), 384 (18), 245 (45), 95 (95), 59 (95). 10a (2α-OH): $^1$H NMR (CDCl$_3$, 500 MHz) δ 0.55 (3H, s, 18-H$_3$), 0.94 (3H, d, J=6.5 Hz, 21-H$_3$), 1.22 (6H, s, 26- and 27-CH$_3$). 2.62 (1H. dd, J=13.0, 4.2 Hz), 2.79 (1H, br d, J=12.9 Hz), 2.90 (1H, dd, J=14.3, 4.2 Hz), 3.25 (1H, br m), 3.53 (1H, dd, J=8.4, 2.6 Hz), 3.79 (1 H, br m), 4.10 (1 H, m), 5.81 and 6.38 (1 H and 1 H, each d, J=11.0 Hz, 6- and 7-H).

10b was prepared in the same way as 10a except from the corresponding 7b (Structure not shown). 10b (2β-OH): $^1$H NMR (CDCl$_3$, 500 MHz) δ 0.55 (3H,s, 18-H$_3$), 0.94 (3H, d, J=6.8 Hz, 21-H$_3$), 1.22 (6H, s, 26- and 27-CH$_3$), 2.79 (1H, br d, J=13.0 Hz), 3.36 (2H, br m), 3.49 (1H, m), 3.68 (1 H, br m), 4.08 (1 H, m), 5.84 and 6.29 (1 H and 1 H, each d, J=11.3 Hz, 6- and 7-H).

EXAMPLE 2

Scheme III illustrates the preparation of 1α,25-dihydroxy-2α-(3'-hydroxypropoxy)-19-nor-vitamin D$_3$ (14a) and 1α,25-dihydroxy-2α(benzyloxy)-19-nor-vitamin D$_3$ (16a).

(a) 19-Nor-(1α,3β)-[bis.(tert.-butyldimethylsilyloxy)-25-triethylsilyloxy-2α-hydroxyvitamin D$_3$ (11a).

10 mg 9a was stirred for 4.5 h at room temperature with 3 ml of a mixture of tetrahydrofuran-acetic acid-water (8:8:1). Ethyl acetate was added and washed with ice cold water, ice cold 10% NaHCO$_3$ solution until neutral, water and brine, and dried over anh. MgSO$_4$, filtered and evaporated. The residue was purified by HPLC (Zorbax Sil 10×25 cm column, 5% ethyl acetate in hexane) to give (in order of peak elutions) 1.2 mg unchanged starting material (12%), 3.5 mg of the expected 2-hydroxy compound 11a, (38%) and 0.75 mg of 25-hydroxy compound (10%) (total recovery 60%). 11a (2α-OH): $^1$H NMR (CDCl$_3$, 500 MHz) δ 0.06, 0.07, 0.08, 0.10 (each 3H, each s, 4× SiMe), 0.55 (3H, s, 18-H$_3$), 0.56 (6H,q, J=7.8 Hz, 3× SiCH$_2$) 0.87 and 0.88 (9H and 9H, each s, 2 × Si-t-Bu), 0.93 (3H, d, J=6.4 Hz, 21-H$_3$), 0.95 (9H, t, J=7.8 Hz, 3 × SiEt), 1.19 (6H, br s, 26- and 27-CH$_3$), 2.27 (1H, d, J=3.3 Hz, OH), 2.79 (1H, dd, J=12.3, 4.2 Hz, 9β-H), 3.51 (1H,dt, J~6 and 3 Hz; after D$_2$O: dd, J=5.8, 2.7 Hz, 2β-H), 3.91 (1H, dt, J=4.3, 5.8 Hz, 3α-H), 4.00 (1H,~dt, J~7.5, 3 Hz, 1β-H), 5.80 and 6.16 (1H and 1H, each, d, J=11.2 Hz, 6- and 7-H). 19-Nor-(1α,3β)-[bis (tert.-butyldimethylsilyloxy)-25-triethylsilyloxy-2β-hydroxy-vitamin D$_3$ (11b) 11b (not shown) was prepared the same as 11a except from 9b (not shown) 11b (2β-OH): $^1$H NMR (CDCl$_3$, 500 MHz) δ 0.06, 0.07, 0.08, 0.10 (each 3H, each s, 4× SiMe), 0.54 (3H, s, 18-H$_3$), 0.56 (6H, q, J=8.0 Hz, 3× SiCH$_2$), 0.86 and 0.89 (9H and 9H, each s, 2× Si-t-Bu), 0.93

(3H, d, J=6 Hz, 21-H₃), 0.94 (9H, t, J=8.0 Hz, SiEt), 1.19 (6H, br s, 26- and 27-CH₃), 2.81 (1H, br d, J~13 Hz, 9β-H), 3.59 (1H, narrow m, after D₂O: dd, J=3.6, 3.3 Hz, 2α-H), 4.00 (2H, m, 1β- and 3α-H), 5.80 and 6.19 (1H and 1H, each d, J=11.0 Hz, 6- and 7-H).

(b) 3-Bromo-1-(tert.-butyldimethylsilyloxy)-propane (12).

1.4 g (1 mmol) 3-bromo-1-propanol was dissolved in 5 ml of anhydrous dimethyl formaide and 3.0 g of imidazole, followed by 3.3 g of tert.-butyldimethylsilyl chloride was added at 0° C. with stirring. The mixture was stirred at room temperature for 2 h. Ether was added, and the ether phase washed with water and brine, dried over anh. MgSO₄, filtered and evaporated. The residue was passed through a small silica gel column and eluted with hexane to give 2.03 g (80%) pure 12. ¹H NMR (CDCl₃, 500 MHz) δ 0.06 (6 H,s, SiMe₂), 0.90 (9H, s, Si-t-Bu), 2.03 (2H, ~quint., J~6 Hz, C-CH₂-C), 3.51 (2H, t, J=6.2 Hz, CH₂-O), 3.73 (2H, t, J=5.8 Hz, CH₂-Br).

(c) 19-Nor-2α(3'-hydroxypropoxy)-1α,25-dihydroxyvitamin D₃ (14a).

1.6 mg (2 μmol) 11a was dissolved in 200 μl of anh. dimethyl formamide and 3 mg sodium hydride (as 60% oil dispersion) followed by 3 mg 18-Crown-6 and 5 μl of the bromo compound 12 was added and the mixture stirred under argon atmosphere for 48 h. The mixture was extracted with ethyl acetate, washed with water, dried over anh. MgSO₄, filtered and evaporated. The residue was passed through a silica gel SepPak column and evaporated in AcOEt. 13a: ¹H NMR (CDCl₃, 500 MHz) δ 0.04, 0.05, 0.06, 0.07 (6H, 6H, 3H, 3H, each s, 6× SiMe), 0.55 (3H, s, 18-H₃), 0.56 (6H, q, J=7.5 Hz, 3× SiCH₂) 0.87 and 0.88 and 0.89 (9H, 9H and 9H, each s, 3× Si-t-Bu), 0.93 (3H, d, J=6 Hz, 21-H₃), 0.95 (9H, t, J=7.5 Hz, 3 × SiEt), 1.19 (6H, br s, 26- and 27-CH₃), 2.79 (1H, br d, J=14 Hz), 3.12 (1H, m), 3.4–4.1 (at least 7H, complex m), 5.80 and 6.12 (1H and 1H, each d, J=11 Hz, 6- and 7-H). The residue was dissolved in 1 ml of anh. tetrahydrofuran and 0.5 ml tetrabutylammonium fluoride (1.0M in THF) was added and stirred under argon atmosphere for 20 h. The residue was extracted with ethyl acetate, washed with water and 10% NaHCO₃ solution, water and brine, and dried over anh. MgSO₄, filtered and evaporated. The residue was passed through a silica gel SepPak column in 1:1 2-PrOH-hexane and purified by HPLC (Zorbax Sil 10 mm×25 cm column, 40% 2-PrOH-hexane) to give 202 μg of the expected product 14a (overall yield from 11a 21%) and 20 μg of 10a. 14a UV (in EtOH) ) λ$_{max}$: 243, 251.5, 261 nm. Mass spectrum (exact mass calcd for C₂₉H₅₀O₅ 478.3658, found 478.3659), m/e (relative intensity) 478 (M+, 5), 460 (6), 442 (2), 402 (4), 384 (3), 245 (15), 184 (20), 142 (100), 95 (50), 59 (38). ¹H NMR (CDCl₃, 500 MHz) δ 0.55 (3H, s, 18-H₃), 0.93 (3H, d, J=6.8 Hz, 21-H₃), 1.22 (6H, s, 26-and 27-H₃), 3.3–4.2 (at least 7H, complex m), 5.83 and 6.34 (1H and 1H, each d, J=11.2 Hz, 6- and 7-H).

(d) 19-Nor-2β(3'-hydroxypropoxy)-1α,25-dihydroxyvitamin D₃ (14b) (Structure not shown)

14b was prepared in the same way as 14a except from the corresponding 11b (structure not shown). 14b UV (in EtOH) λ$_{max}$: 243, 251.5, 261 nm. Mass spectrum m/e (relative intensity) 478 (M+, 5), 460 (20), 442 (18), 424 (4), 384 (3), 245 (28), 181 (28), 95 (50), 69 (100), 59 (68). ¹H NMR (CDCl₃, 500 MHz) δ 0.54 (3H, s, 18-H₃), 0.94 (3H, d, J=6.5 Hz, 21-H₃), 1.22 (6H, s, 26- and 27-H₃), 2.79 (1H, br d, J~12 Hz, 9β-H), 3.0–4.3 (at least 7H, complex m), 5.83 and 6.29 (1H and 1H, each d, J=11.2 Hz, 6- and 7-H).

(e) 19-Nor-2α(benzyloxy)-1α,25-dihydroxyvitamin D₃ (16a).

1.6 mg (2 μmol) (11a) was dissolved in 200 μl of anh. dimethyl formamide and 3 mg sodium hydride (as 60% oil dispersion) followed by 3 mg 18-Crown-6 and 6 μl of benzylbromide benzene solution, (prepared from 120 μl benzylbromide in 1 mL benzene) was added and the mixture stirred under argon atmosphere for 48 h. The mixture was extracted with ethyl acetate, washed with water, dried over anh. MgSO₄, filtered and evaporated. The residue was passed through a silica gel SepPak column, evaporated to give 860 μg crude 15a, which was without purification deprotected. 860 μg crude 15a was dissolved in 200 μL of methanol and 10 mg methanol washed AG-50W-X4 cation exchange resin added. The mixture was stirred under argon atmosphere at RT for 18 h, filtered through a SepPak Silica cartridge and washed with 2-propanol. The solvent was evaporated under reduced pressure and the residue purified by HPLC (Zorbax Sil 10 mm×25 cm column, 30% 2-PrOH-hexane mixture) to give 170 μg of the 2α-benzyloxy-compound mixture) to give 170 μg of the 2α-benzyloxy-compound 16a. 16a: UV (in EtOH) λ$_{max}$: 243, 251.5, 261 nm. Mass spectrum (exact mass calcd for C₃₃H₅₀O₄ 510.3709 found 510.3703), m/e relative intensity 510 (11), 492 (8), 474 (2), 401 (8), 91 (100). ¹H NMR (CDCl₃, 500 MHz) δ 0.55 (3 H, s, 18-H₃), 0.93 (3 H, d, J=6.7 Hz, 21-H₃), 1.22 (6H, s, 26- and 27-H₃), 2.79 (2H, m), 3.45 (1 H, dd, J=7.3, 3.0 Hz, 2β-H), 3.97 (1 H, m, 3α-H), 4.11 (1 H, m, 1β-H), 4.65 and 4.72 (1 H and 1 H, each d, J=11.8 Hz, O-CH₂'), 5.83 and 6.33 (1 H and 1 H, each d, J=11.2 Hz, 6- and 7-H), 7.2–7.4 (5H, br m, Ar-H).

SCHEME I

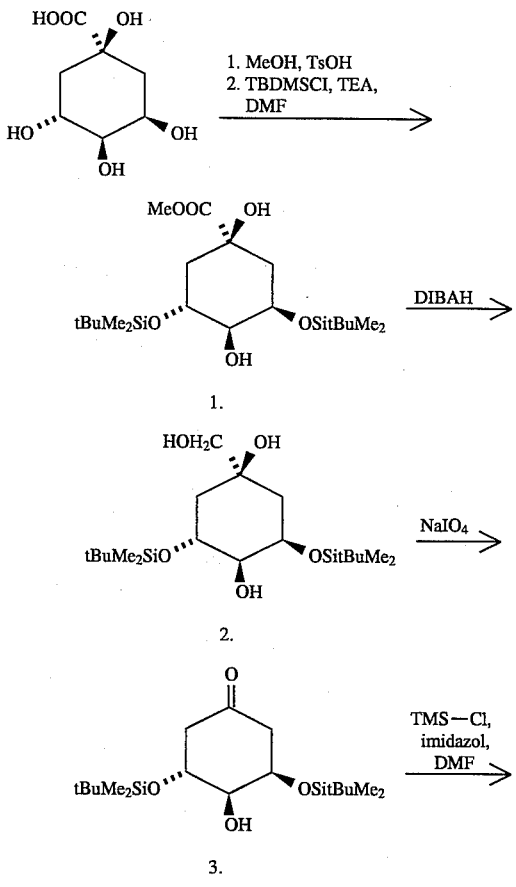

5,536,713
11
-continued
SCHEME I
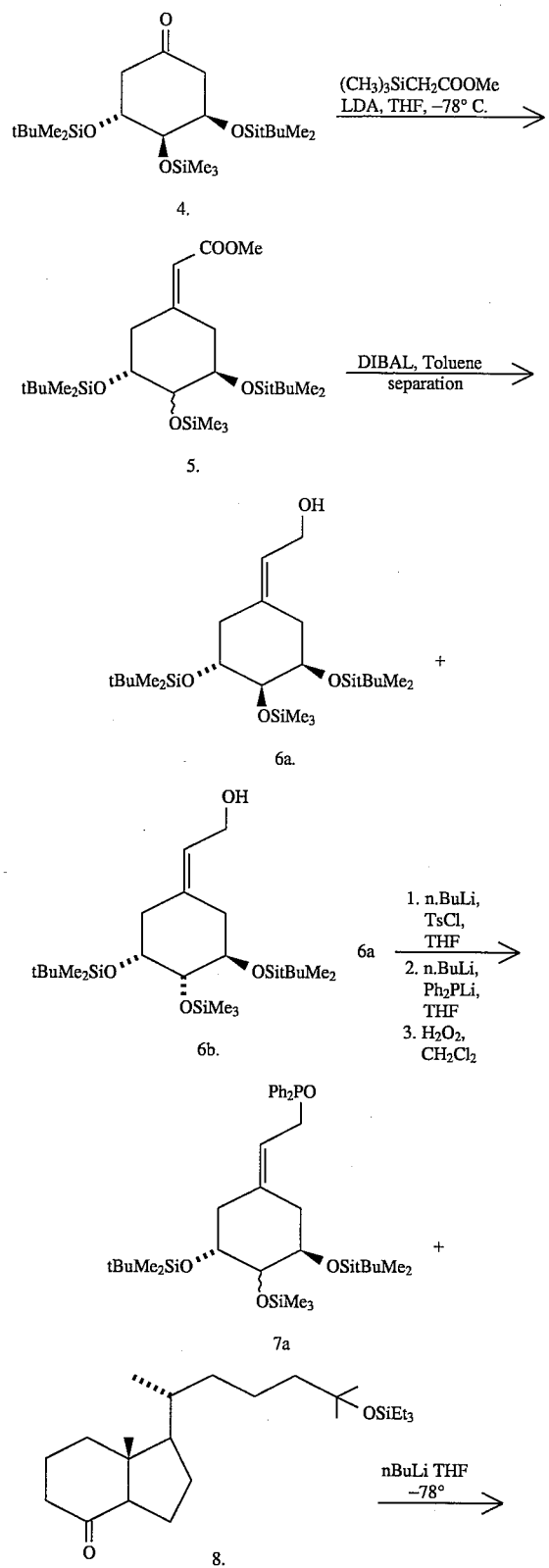
12
-continued
SCHEME I
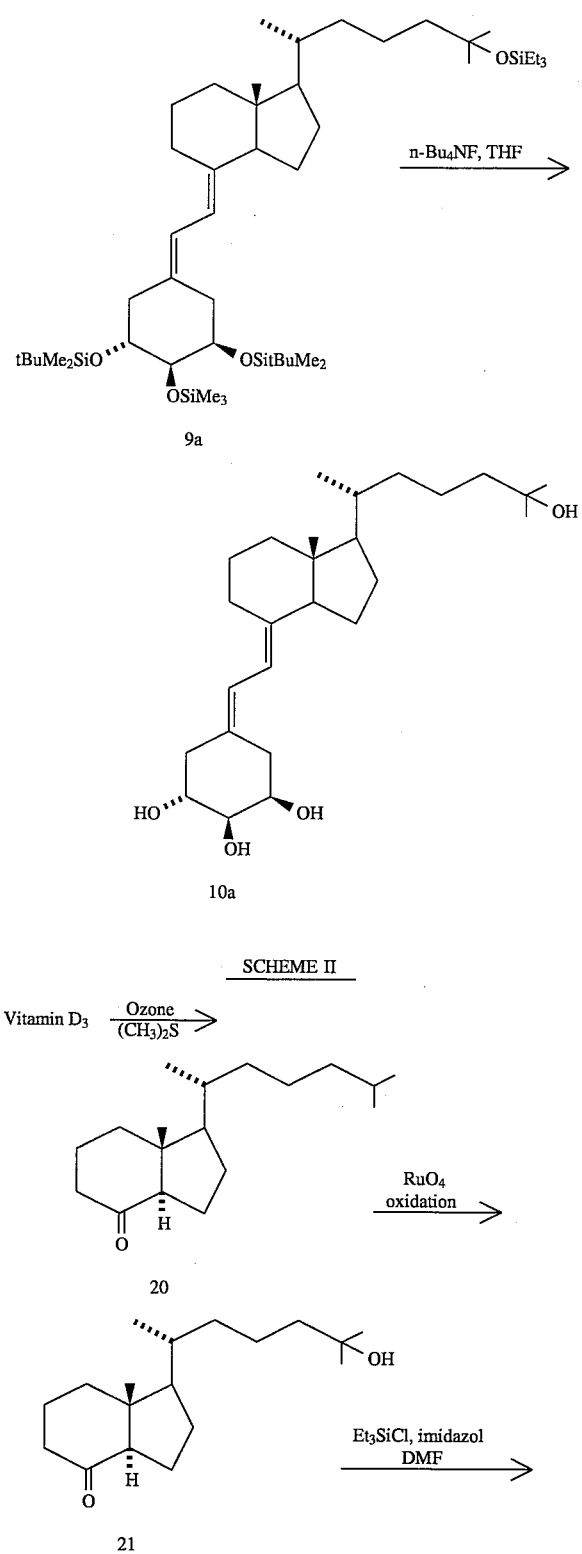

-continued
SCHEME II
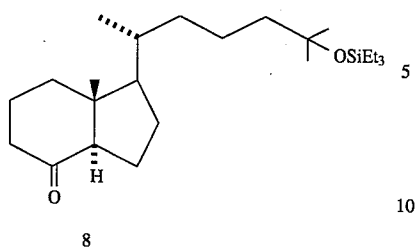
8
SCHEME III
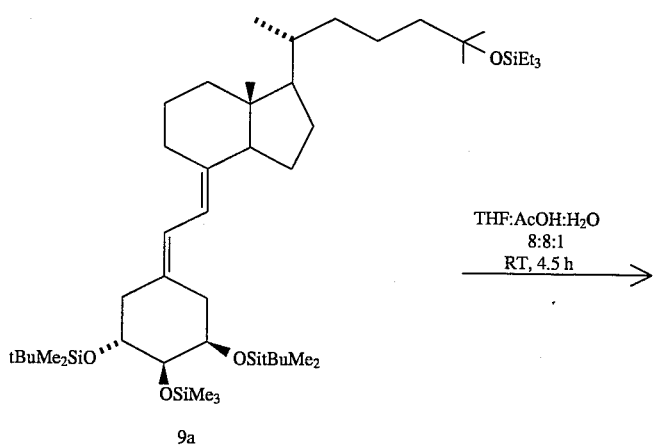
9a
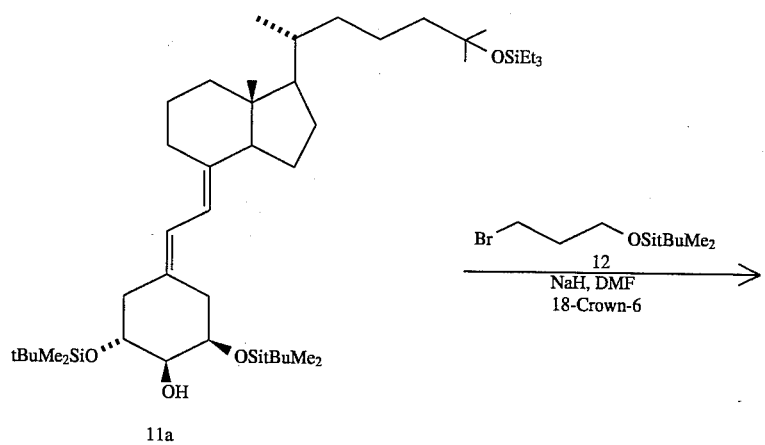
11a
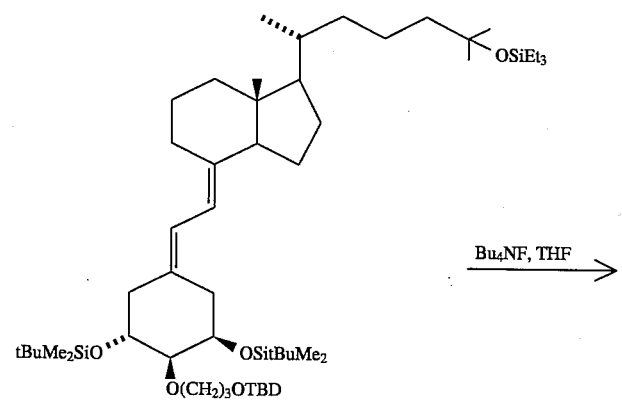
13a -continued
SCHEME III
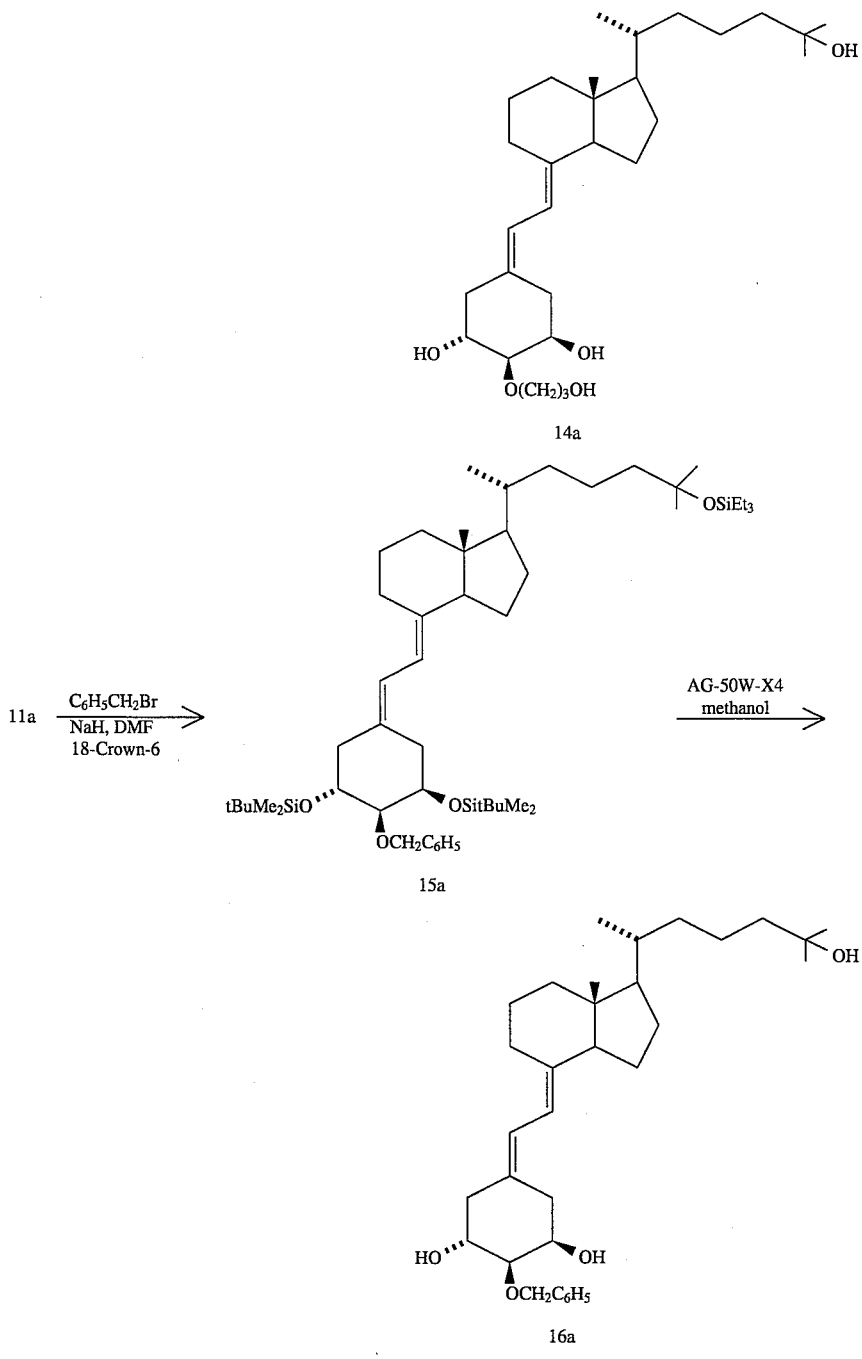
SCHEME IV
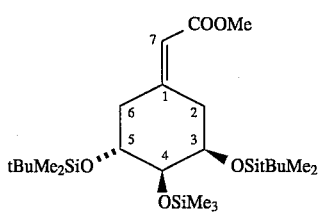
-continued
SCHEME IV

17

-continued
SCHEME IV

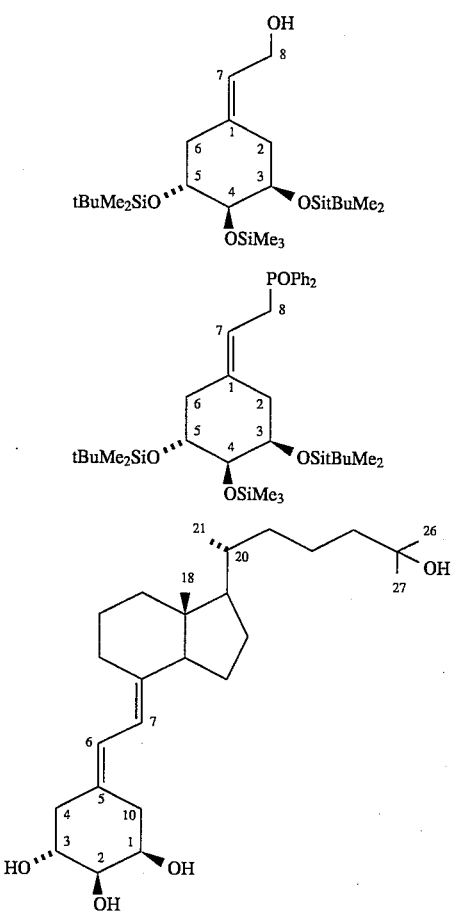

Biological Activity of 1α-Hydroxy-19-Nor Vitamin D Compounds

Figure 1B:
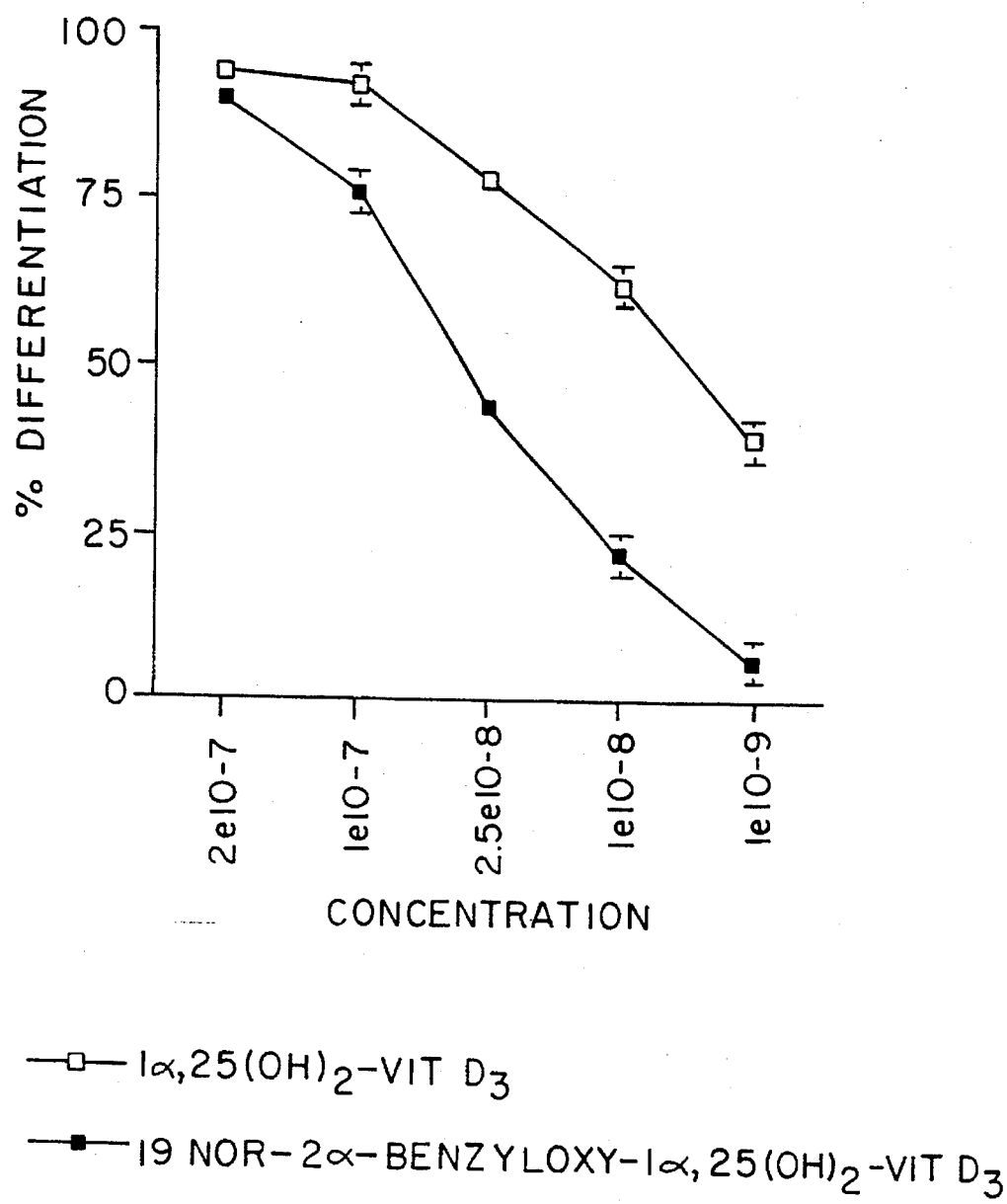

The novel compounds of this invention exhibit an unexpected pattern of biological activity. All of the 19-nor compounds exhibited high potency in promoting the differentiation of malignant cells. The two 2-hydroxy analogs showed in vivo calcium transport with little or no bone calcium mobilization; the 2β- more than the 2α- analog; while the 2α-hydroxypropoxy analog showed a selective activity profile, combining high potency in inducing differentiation of malignant cells with very low bone calcium mobilizing activity. This is illustrated by the biological assay results obtained for the claimed 19-nor-vitamin $D_3$ compounds, which are summarized in FIGS. 1 and 2, and Table 1. FIG. 1 shows a comparison of the activity of the known active metabolite 1α,25-dihydroxyvitamin $D_3$ and two of the 19-nor analogs in inducing the differentiation of human leukemia cells (HL-60 cells) in culture to normal cells (monocytes). Differentiation activity was assessed by a standard differentiation assay, abbreviated in FIG. 1 as NBT (nitroblue tetrazolium reduction). The assay was conducted according to known procedures, as given, for example, by DeLuca et al U.S. Pat. No. 4,717,721 and Ostrem et al, J. Biol. Chem. 262, 14164, 1987. For the assay, the differentiation activity of the test compounds is expressed in terms of the percent of HL-60 cells having differentiated to normal cells in response to a given concentration of test compound.

The results summarized in FIG. 1 clearly show that the new analogs, 1α,2α,25-trihydroxy-19-nor-vitamin $D_3$ and

18

1α,25-dihydroxy-2α-(3'-hydroxypropoxy)-19-nor-vitamin $D_3$, are as potent as 1α,25-dihydroxyvitamin $D_3$ in promoting the differentiation of leukemia cells. Thus in NBT assay close to 90% of the cells are induced to differentiation by 1α,25-dihydroxyvitamin $D_3$ at a concentration of $1 \times 10^{-7}$ molar, and the same degree of differentiation is achieved by the two 19-nor analogs.

Figure 2A:
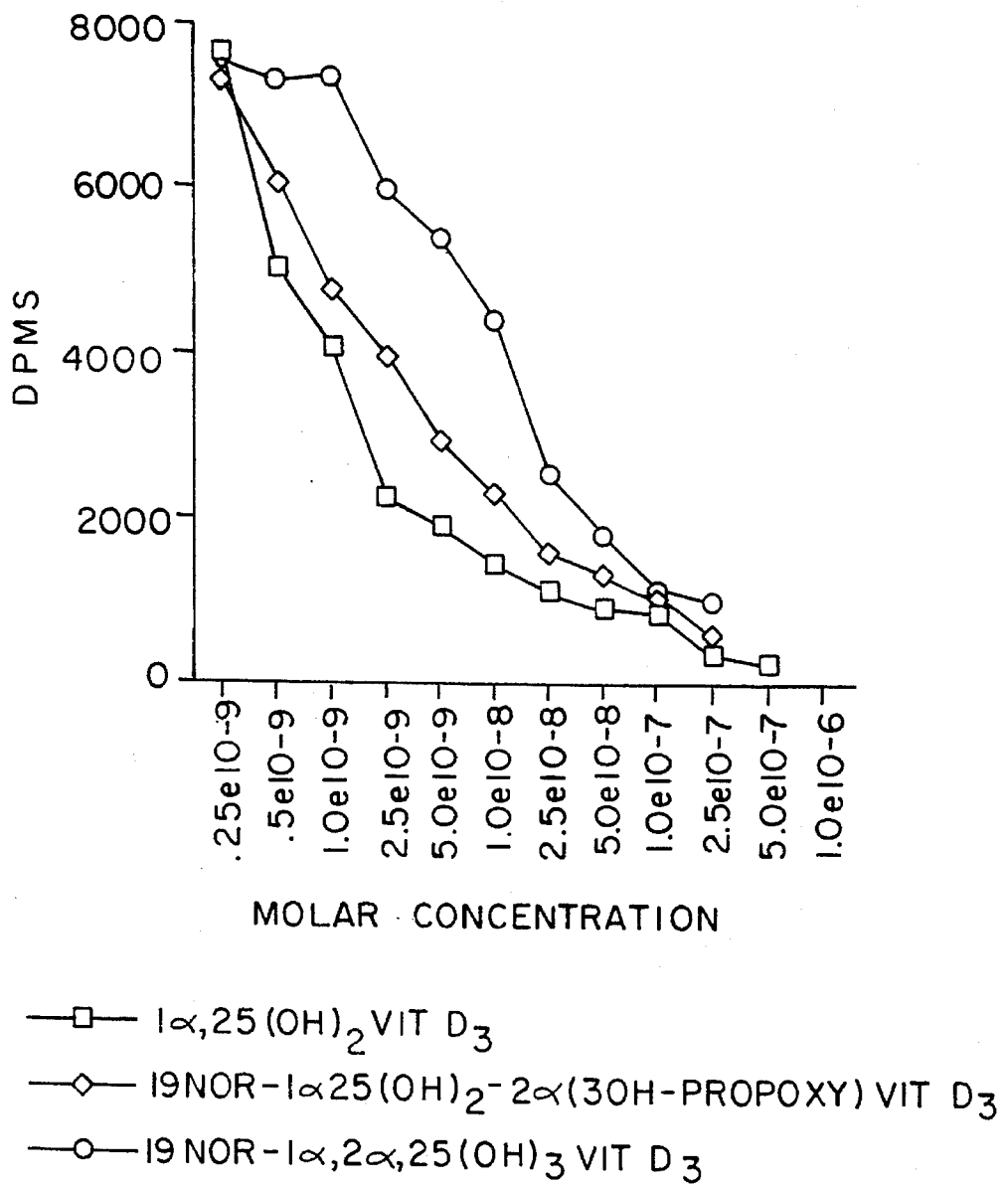
FIGS. 2a and 2b are graphs of the competitive binding ability versus concentration for the same four compounds as in FIGS. 1a and 1b.
Figure 2B:
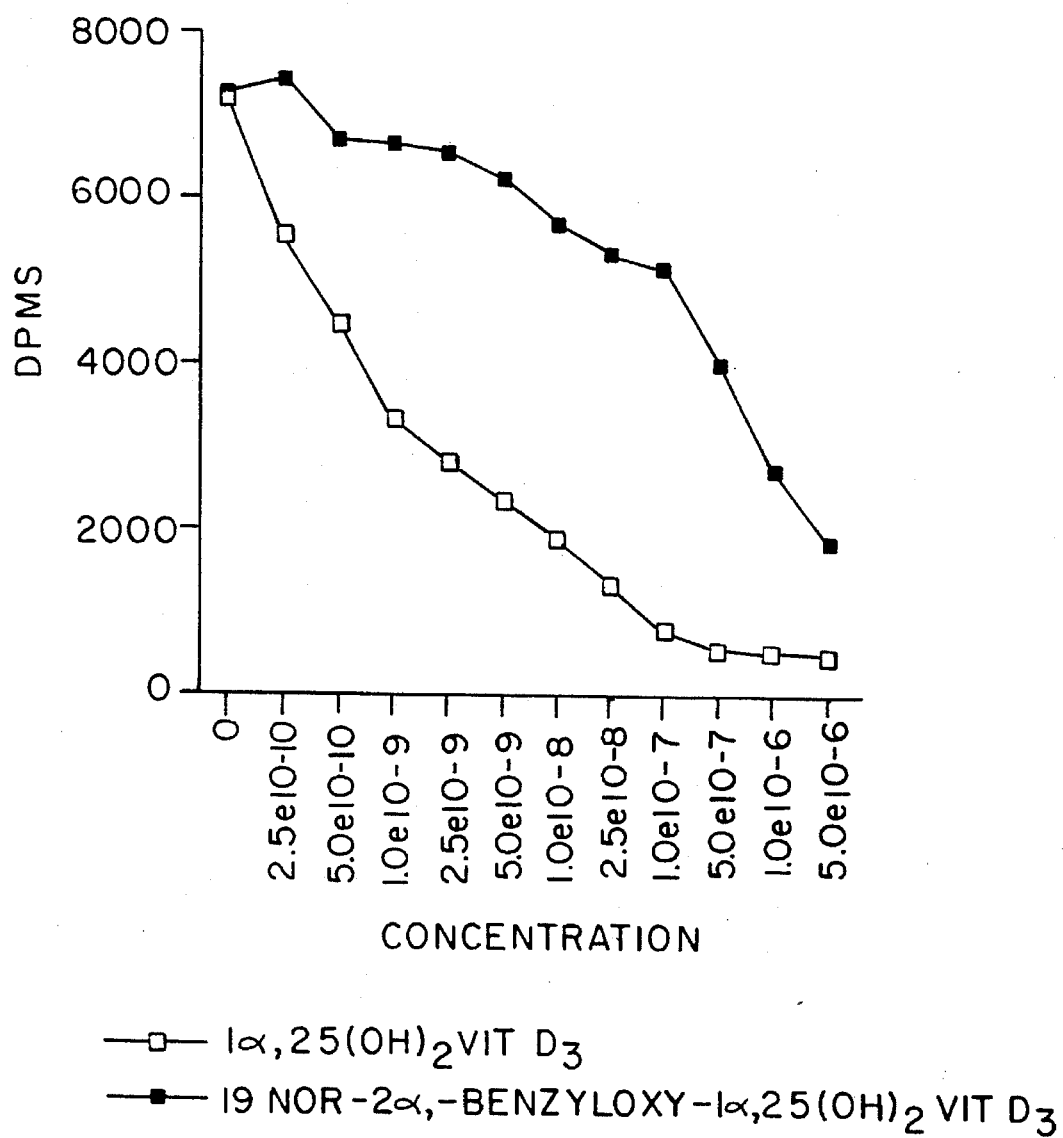

FIG. 2 shows a comparison of the same three compounds as in FIG. 1 illustrating their relative activity with regard to competitive binding to the vitamin D receptor. The competitive receptor binding was done with pig nuclear extract as described in Periman et al. Biochemistry 29, 190–196 (1990) using the porcine extract prepared as described by Dame et al PNAS 82, 7825–7829 (1985). These data are used to demonstrate that the compounds described herein have relatively high in vivo activity, and have somewhat less activity than $1,25-(OH)_2D_3$ in binding to the vitamin D receptor.

In regard to the biological data on the calcemic activity of these compounds reported in Table 1, Holtzmann weanling rats were maintained on 0.47% Ca, 0.3% P, for one week, then switched to a low Ca diet (0.02% Ca) for an additional three weeks. During the 4th week all animals were dosed with the appropriate compounds via the peritonal cavity. All doses were suspended in ethanol propylene glycol (5/95) and administered daily for seven days. None of the compounds produced hypercalcemia over the seven day dosing period. The 19-nor-2α-hydroxypropoxy-1α,25-dihydroxyvitamin $D_3$ did mobilize small amounts of Ca from bone at 130 or 325 pmole daily. However, these levels could easily be controlled by lowering the dose and the activity in this regard was far below that of the standard compound, 1,25 $(OH)_2D_3$.

The data in Table 1 illustrates that 19-nor-1α,2α,25-trihydroxyvitamin $D_3$ has biological activity in intestinal transport similar to that of $1,25-(OH)_2D_3$ but possesses little or no bone calcium mobilizing activity even when given at 325 pmol/day. Similarly, the 1α,2β,25-trihydroxyvitamin $D_3$ compound has considerable activity in intestinal calcium transport but again lacks bone calcium mobilizing activity. On the other hand, the 19-nor-2α-hydroxypropoxy-1α,25-dihydroxyvitamin $D_3$ compound has an activity profile similar to $1,25-(OH)_2D_3$ but has preferential activity on bone calcium mobilization.

The 2-propoxy compound would be useful in circumstances where an increased bone turnover is desirable such as low bone turnover osteoporosis. The other two compounds would find utility as a treatment for postmenopausal and senile osteoporosis because of their low bone calcium mobilizing activity with normal differentiative activity, normal binding to the receptor, and normal calcium transport activity. The compounds that could be considered for anticancer or psoriasis might be the 2α- and 2β-hydroxy compounds because of their tendency to not cause hypercalcemia.

For treatment purposes, the novel compounds of this invention can be formulated as solutions in innocuous solvents, or as emulsions, suspensions or dispersions in suitable innocuous solvents or carriers, or as pills, tablets or capsules, containing solid carriers according to conventional methods known in the art. For topical applications the compounds are advantageously formulated as creams or ointments or similar vehicle suitable for topical applications. Any such formulations may also contain other pharmaceutically-acceptable and non-toxic excipients such as stabilizers, anti-oxidants, binders, coloring agents or emulsifying or taste-modifying agents.

The compounds are advantageously administered by injection, or by intravenous infusion of suitable sterile solutions, or in the form of oral doses via the alimentary canal, or topically in the form of ointments, lotions, or in suitable transdermal patches. For the treatment of malignant diseases, the 19-nor-vitamin D compounds of this invention are administered to subjects in dosages sufficient to inhibit the proliferation of malignant cells and induce their differentiation into normal monocyte-macrophages. Suitable dosage amounts are from 1 to 500 µg of compound per day, such dosages being adjusted, depending on the disease to be treated, its severity and the response or condition of the subject as is well-understood in the art.

TABLE 1

| Group | Amount pmoles/d/ 7 days | S/M Ratio ave. s.e.m. | Serum Ca ave. s.e.m. (mg %) |
|---|---|---|---|
| D-Deficient | 0 | $^a$2.1 ± 0.18 | $^a$4.3 ± 0.14 |
| 1α,25-(OH)$_2$D$_3$ | 130 | $^b$8.0 ± 0.80 | $^b$5.6 ± 0.20 |
| 19-Nor-1α,2α, 25-(OH)$_3$ D$_3$ | 130 325 | $^c$5.3 ± 0.26 5.0 ± 0.14 | 1$^{ca}$4.12 ± 0.3 $^{cb}$4.14 ± 0.10 |
| D-Deficient | 0 | $^a$3.0 ± 0.8 | $^a$4.3 ± 0.23 |
| 19-Nor-1α,2β, 25-(OH)$_3$D$_3$ | 65 325 650 | $^c$5.8 ± 0.22 10.8 ± 0.39 9.9 ± 0.45 | 2$^{ca}$4.2 ± .19 $^{cb}$4.2 ± 0.28 $^{cc}$4.3 ± 0.24 |
| 1α,25-(OH)$_2$D$_3$ | 65 325 | $^b$8.3 ± 0.32 10.5 ± 1.2 | $^{b1}$5.2 ± 0.16 $^{b2}$6.8 ± 0.24 |
| D-Deficient | 0 | $^a$2.5 ± 0.15 | $^a$4.3 ± 0.13 |
| 1α,25-(OH)$_2$D$_3$ | 130 325 | $^b$7.1 ± 0.49 7.8 ± 0.60 | $^{b1}$5.7 ± 0.23 $^{b2}$7.1 ± 0.30 |
| 19-Nor- 2α-hydroxy- propoxy- 1α,25-(OH)$_2$D$_3$ | 130 325 | $^c$3.5 ± 0.23 4.3 ± 0.33 | 3$^{ca}$4.9 ± 0.11 $^{3b}$5.8 ± 0.20 |

Statistical data
Serosal/Mucosal
Panel 1 All from a
P < .001
Panel 2 All from a
P < .001
Panel 3 All from a
P < .001

Serum Ca
Panel 1, b from a P < .001
$^1$c$^a$, c$^b$ from a N.S.
Panel 2, b$^1$, b$^2$, from a p < .001
$^2$c$^a$c$^b$c$^c$ N.S.
Panel 3 b$^1$, b$^2$ from a p < .001
(3) c$^a$ from a p < .0005
c$^b$ from a, p < .001

We claim:
1. A vitamin D compound having the structure:

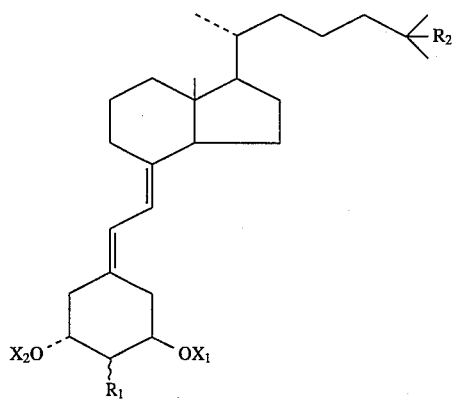

where $X_1$ and $X_2$ are each selected from hydrogen or a hydroxy protecting group, $R_1$ which may be in either α or β position is a hydroxy group, protected hydroxy group or the group $OR_3$ where $R_3$ is an alkyl, hydroxyalkyl, fluoroalkyl, arylalkyl or aryl group, and $R_2$ is hydrogen or a hydroxy group.

2. A pharmaceutical composition comprising a 19-nor-vitamin D compound as defined in claim 1 together with a pharmaceutically acceptable excipient.

3. The pharmaceutical composition of claim 2 wherein said 19-nor-vitamin D compound is 1α,2α,25-trihydroxy-19-nor-vitamin D$_3$.

4. The pharmaceutical composition of claim 2 wherein said 19-nor-vitamin D compound is 1α,2β,25-trihydroxy-19-nor-vitamin D$_3$.

5. The pharmaceutical composition of claim 2 wherein said 19-nor-vitamin D compound is 1α,25-dihydroxy-2α-(3'-hydroxypropoxy)-19-nor-vitamin D$_3$.

6. The pharmaceutical composition of claim 2 wherein said 19-nor-vitamin D compound is 1α,25-dihydroxy-2β-(3'-hydroxypropoxy)-19-nor-vitamin D$_3$.

7. The pharmaceutical composition of claim 2 wherein said 19-nor-vitamin D compound is 1α,25-dihydroxy-2β-(benzyloxy)-19-nor-vitamin D$_3$.

8. 1α,2α,25-trihydroxy-19-nor-vitamin D$_3$.

9. 1α,2β,25-trihydroxy-19-nor-vitamin D$_3$.

10. 1α,25-dihydroxy-2α-(3'-hydroxypropoxy)-19-nor-vitamin D$_3$.

11. 1α,25-dihydroxy-2β-(3'-hydroxypropoxy)-19-nor-vitamin D$_3$.

12. 1α,25-dihydroxy-2α-(benzyloxy)-19-nor-vitamin D$_3$.

13. A method of treating osteoporosis comprising administering to a patient an effective amount of a vitamin D$_3$ compound selected from the group consisting of 1α,2α,25-trihydroxy-19-nor-vitamin D$_3$, 1α,2β,25-trihydroxy-19-nor-vitamin D$_3$, 1α,25-dihydroxy-2α-(3'-hydroxypropoxy)-19-nor-vitamin D$_3$, 1α,25-dihydroxy-2β-(3'-hydroxypropoxy)-19-nor-vitamin D$_3$, 1α,25-dihydroxy-2α-(benzyloxy)-19-nor-vitamin D$_3$ and mixtures thereof.

14. The method of claim 13 wherein the 19-nor-vitamin D$_3$ compound is administered in an amount of from about 1 µg to about 500 µg per day.

15. The method of claim 13 wherein the osteoporosis is senile osteoporosis.

16. The method of claim 13 wherein the osteoporosis is postmenopausal osteoporosis.

17. The method of claim 16 wherein the 19-nor-vitamin D$_3$ compound is administered to women during and subsequent to menopause.

18. The method of claim 16 wherein the 19-nor-vitamin D$_3$ compound is administered to women prior to the onset of menopause.

19. The method of claim 13 wherein the 19-nor-compound, in solution in a liquid vehicle ingestible by and nontoxic to said patient, is administered orally in encapsulated form.

20. The method of claim 13 wherein the 19-nor-vitamin D$_3$ compound is administered in a slow release formulation.

21. The method of claim 13 wherein the 19-nor-vitamin D$_3$ compound is administered daily in divided dosages.

22. The method of claim 13 wherein the osteoporosis is low bone turnover osteoporosis.

* * * * *

UNITED STATES PATENT AND TRADEMARK OFFICE
CERTIFICATE OF CORRECTION

PATENT NO. : 5,536,713
DATED : July 16, 1996
INVENTOR(S) : Hector F. DeLuca et al It is certified that error appears in the above-indentified patent and that said Letters Patent is hereby corrected as shown below:

IN THE CLAIMS:

CLAIM 7　　　　　　　　Delete "2β" and substitute therefor ---2α---.
Col. 20, line 21
(Claim 12, line 2)

Signed and Sealed this

Seventh Day of January, 1997

*Attest:*

BRUCE LEHMAN

*Attesting Officer*　　　*Commissioner of Patents and Trademarks*